United States Patent [19]

Revel et al.

[11] 4,302,533

[45] Nov. 24, 1981

[54] NOVEL ASSAYS FOR INTERFERON

[75] Inventors: Michel Revel, Rehovot; Adi Kimchi, Raanana; Lester Shulman; David Wallach, both of Rehovot, all of Israel

[73] Assignee: Yeda Research & Development Co. Ltd., Rehovot, Israel

[21] Appl. No.: 139,697

[22] Filed: Apr. 11, 1980

[30] Foreign Application Priority Data

Apr. 22, 1979 [IL] Israel .................................. 57108

[51] Int. Cl.$^3$ ..................... C12Q 1/02; C12Q 1/68
[52] U.S. Cl. ........................................ 435/4; 435/6; 435/15; 435/29; 435/811; 424/85; 23/230 B
[58] Field of Search ............ 435/810, 811, 4, 6, 435/15, 29; 424/85; 23/230 B

[56] References Cited

U.S. PATENT DOCUMENTS 3,910,824 10/1975 Cartwright et al. ............... 435/811
4,061,538 12/1977 Dorner et al. ........................ 424/85

OTHER PUBLICATIONS

Revel, M. "Molecular Mechanisms Involved in the Antiviral Effects of Interferon", *Interferon 1* 1979, Grosser, I., Editor-In-Chief, Academic Press, pp. 14–151.

Kimchi, A. et al. "Kinetics of the Induction of Three Translation Regulatory Enzymes by Interferon", *Proc. Natl. Acad. Sci. USA*, vol. 76, pp. 3208–3212, Jul. 1979.

Zilberstein A. et al. "Specific Phosphorylation in Vitro of a Protein Associated with Ribosomes of Interferon--Treated Mouse Cells" *FEBS Letters*, vol. 68 #1, Sep. 1976 North-Holland Publishing Co.-Amsterdam.

Zilberstein, A. et al. "Isolation of two Interferon-Induced Translational Inhibitors: A protein Kinase and an Oligo–Isoadenylate Synthetase," *Proc. Natl. Sci. USA*, vol. 75, #10, pp. 4734–4738, Oct. 1978.

*Primary Examiner*—Benoit Castel
*Attorney, Agent, or Firm*—Browdy and Neimark

[57] ABSTRACT

The present invention relates to an assay for the quantitative determination of interferon which comprises extracting a cell previously exposed to said interferon with an extractant, and determining in such extract the quantity of an enzyme the content of which in said cell is a function of the quantity of interferon to which said cell had been previously exposed and to a kit for carrying out such assay.

5 Claims, No Drawings

NOVEL ASSAYS FOR INTERFERON

FIELD OF THE INVENTION

The invention relates to a novel assay for the quantitative determination of interferons in body fluids, body tissues, in cell cultures, in cultivation media and the like. The invention further relates to means, preferably in kit form, for carrying out such assays. Other and further features of the invention will become apparent hereinafter.

BACKGROUND OF THE INVENTION

Interferons are glycoproteins that produce in cell cultures a reduction in virus multiplication. This antiviral activity makes them promising agents in the treatment of viral diseases in man. Interferons are also considered as possible anti-cancer agents. Assays of interferons were done, until now, by measuring the reduction of the growth of a certain virus, in cells exposed to interferon. These assays are time-consuming and variable because of the need for virus infection.

Assays for interferon previously described are based on a pretreatment of cells with interferon for 10-20 hours, followed by infection with a test virus for at least 8-10 hours, and usually 24-48 hours. A viral product or a cytopathic effect is then measured. The need to infect the cells introduces an additional variable and requires additional controls in the test.

SUMMARY OF THE INVENTION

The present invention relates to a novel assay for the quantitative determination of interferon, and to means for carrying out such assays. The assay is based on the discovery that when interferon is added to cell cultures, the content of certain specific enzymes is increased. This increase, under controlled conditions, is indicative of the quantity of interferon. The assay can also be effected on cells, such as white blood cells, and specifically on human leukocytes, and the content of certain enzymes is a measure of the previous exposure of said cells to interferon which has taken place in the human body.

The assay is carried out with very small quantities of enzymes and the test is a very sensitive and accurate one.

There exists a number of enzymes the quantity of which is a function of cell exposure to interferons. In the presence of interferon the quantity of said enzymes is increased. The increase is a gradual one, and starts after an induction period of a few hours. After about 3 hours under physiological conditions an increase can be measured and this reaches a peak after from about 12 to 24 hours. When the assay is performed under controlled conditions it is advantageous to measure the quantity of the enzyme which is being determined after about 8 hours. Other periods of time can be chosen. The presence of interferon results in an increase of the quantity of the following enzymes:

1. A protein kinase which phosphorylates specifically the small sub-unit of initiation factor EIF2;
2. Oligo-isoadenylate synthetase that produces from ATP a specific oligonucleotide (2'-5') pppApApA;
3. A phosphodiesterase that degrades (2'-5') dinucleoside monophosphates such as (2'-5') ApA.

When interferon, or a medium containing it, is added to a cell culture the content of these enzymes in said cells is increased. Also the content of other enzymes which is increased due to interferon can be used for the assay.

When a small quantity of cells of a cell culture previously exposed to interferon is extracted after a predetermined period of time by a suitable extractant, the extract can be assayed for its content of said enzymes contained in said cells, and this quantity of enzyme or enzymes is indicative of the quantity of interferon to which said cells were exposed. The assay can also be performed on leukocytes which are extracted and the enzyme content of which is determined by the specific assay of the invention, which is adapted to measure ultra-small quantities of said enzymes. This content of enzymes is indicative of the exposure to interferons of the cells in the body and this permits definite deductions on the malady of the patient.

The cells to be assayed are extracted by means of a suitable extractant, such as a non-ionic surfactant. A surfactant which was found to be suitable is Nonidet P40 (Polyethylene glycol mono(octylphenyl) ether produced by Paz Company, Israel. The extraction can also be effected by other means. The increase of enzyme content of cell cultures exposed to interferon is a marked one: It differs with the 3 enzymes listed above: it is by a factor of 10 times with enzyme (1); by a factor of up to 20 to 100 times with enzyme (2) and by a factor of 3 times with enzyme (3).

The process of the invention comprises establishing the enzyme content of the sample to be assayed (the enzymes being of the type which increases after exposure of cells to interferon), and deducing from the enzyme content the quantity of the interferon to which said cells were exposed.

The following examples illustrate the determination of interferons via an assay of the three enzymes defined above, the content of which increases in cells after exposure of same to interferons.

As pointed out above, the increase of enzyme content of the cells of a cell culture exposed to interferon is a gradual one, and an appreciable increase can be detected at about 3 hours after exposure. A determination 8 hours after exposure is satisfactory as at this period of time a substantial increase has taken place. The enzyme content reaches a peak after from 12 to 24 hours, depending on the enzyme. When the value is determined after 8 hours, the resulting value can be used to establish the interferon quantity by resorting to a calibration table prepared under identical conditions.

The following Examples are illustrative only and it is to be clear that these are by way of example only. An assay may be based on any other enzyme the quantity of which in cells increases after exposure of such cells to interferon.

DETAILED DESCRIPTION OF THE INVENTION

Example 1: Determination of Interferon by assay of Protein Kinase (PK-i)

Serial dilutions of interferon from 0 to 50 units/ml are prepared in the wells of a plastic microtiter plate (96 wells), in 5 consecutive dilutions at a factor of 1:5 each by dilution in tissue culture medium with 10% calf serum. A freshly trypsinized suspension of mouse L cells or human diploid fibroblast is added. Each well receives ~25,000 cells. The final volume is 0.1 ml. After 8 hours, the medium is drained from the microtiter plate and 0.025 ml of a solution of 0.5% Nonidet P40 in 20 mM Hepes buffer pH 7.5, 5 mM MgCl$_2$, 120 mM KCl, 1 mM dithiothreitol, 10% glycerol is added. After 6–9 minutes, the plate is centrifuged at 4,000 rpm for 5 min in a centrifuge rotor equipped with a proper adaptor. From each well 0.015 ml are withdrawn and 0.5 µg/ml of double stranded polyinosinicpolycytidilic acid poly(-rI):(rC) is added with 0.5 mM ATP. The final volume is 0.02 ml. The mixture is incubated 15 min at 30° C. Five ηg of the protein called eukariotic initiation factor 2 (purified from rabbit reticulocyte by the procedure of Benne et al., J. Biol. Chem. (1976) 251, 7675–81) and 0.075 mM [$^{32}$P]-γ-ATP (16 Ci/mmole) are added, and the incubation is continued for 15 minutes at 30° C. The radioactivity incorporated into protein eIF2 is measured by precipitation in acid or better by electrophoresis of the mixture on a gel of 12% polyacrylamide with 0.1% sodium dodecyl sulfate. The gel is dried and exposed to an X-ray film for a few hours. The film, when developed, shows a band with a molecular weight of 35,000. The intensity of the band is measured by densitometry at 600 nanometer in a recording spectrophotometer. The intensity of the 35,000 Mr band is a direct measure of the amount of $^{32}$P phosphate incorporated into the protein eIF2 and is a measure of protein kinase PK-i activity. Electrophoresis on cellulose acetate can be used as well.

Table 1 shows that an increase in PK-i activity over untreated cells can be seen with 2 units interferon per ml. The lowest concentration of interferon which blocks over 90% of the replication of vesicular stomatitis virus on the cells produces the maximal increase in protein-kinase PK-i activity. Table 2, illustrates a time course of PK-i increase in mouse L cells. The increase starts 3 hours after cells were exposed to interferon and becomes maximal at 24 hours. The half-maximal increase is obtained at 8 hours after interferon treatment.

Example 2: Interferon Assay based on measurements of oligo-isoadenylate and of phosphodiesterase Increases in two other enzymes were measured in the same NP40 extracts of interferon-treated cells: Oligo-isoadenylate synthetase and a 2'-phosphodiesterase. As an example, the measurement of oligo-isoadenylate synthetase E increase after interferon treatment is illustrated. Cells are lysed with NP40 as above and polyinosinic-polycytidilic (double stranded) acids (poly(rI):(rC)) bound to Sepharose beads (by the technique of Wagner et al., Biochem. Biophys. Res. Commun. (1971) 45, 184–189) are added. The beads are washed and suspended in an equal volume (25 µl) of NP40 cell extracts. The non-adsorbed material is removed and the beads pellet incubated in 1 mM [$^{32}$P]α-ATP (3 Ci/mmol), 1 mM dithiothreitol for 20 h at 30° C. The supernatant (10 µl) is treated with 0.35 units bacterial alkaline phosphatase in 30 mM Tris base, for 60 min 37° C. The digest is submitted to paper electrophoresis on Whatman 3 MM paper at 3000 V for 4 hours, or better to thin layer chromatography on polyethyleneimine cellulose with acetic acid. The spots corresponding to (2'-5')ApA and (2'-5')ApApA are cut and counted by scintillation. The increase in oligo-isoadenylate synthetase is expressed as the amount of radioactive phosphate incorporated from [$^{32}$P]-α-ATP into the (2'-5') diadenylate monophosphate or into (2'-5') triadenylate diphosphate or in both.

A more rapid and simpler procedure is to add the digest to small disposable alumina columns (volume of columns 0.3 ml) previously equilibrated in 1 M glycine, 0.75 N HCl buffer (pH 2). A volume of 3 ml of the same buffer is then passed through the column and directly collected in vials suitable for radioactive measurements in a scintillation counter.

The same results are obtained with the human diploid foreskin fibroblasts treated with human fibroblast interferon. The main advantage of this new assay is (1) that it does not depend on virus infection of the cells following interferon treatment; (2) that it is accurate, reproducible and rapid; (3) that it can be used not only to measure the amounts of interferon present in an unknown solution, but also to examine whether cells of a given tissue have reacted to interferon. For example, if interferon is injected into a patient, a blood sample can be taken and it can be determined whether the white blood cells (lymphocytes) contain elevated amounts of protein kinase PK-i. The same determination can be done on a small biopsy sample from the conjuctiva or skin exposed topically to interferon.

Similar measurements were made with phosphodiesterase and analogous results were obtained. The phosphodiesterase is measured using (2'-5')ApA 1 mM as substrate and cell extracts 10 µl. After 30 min at 37° C. the reaction mixture is subjected to thin layer chromatography on polyethyleneimine cellulose with 0.32 M LiCl. The amount of 5'AMP produced is a measure of the phosphodiesterase. 5'AMP is measured by elution with 0.7 M MgCl$_2$ from the cellulose and absorbance measurement at 250 mµ.

Measurements can be done in the same cell extract as measurement of the protein kinase described in Example 1.

Example 3: Level of oligo-isoadenylate synthetase in human blood cells

Assays of the interferon-induced enzymes provides a new and convenient method to determine the biological response of cells or tissues of humans or animals to interferon. As an example, measurements of the oligo-isoadenylate synthetase were performed on blood cells from human donors and of patients in various pathological conditions. A 2 ml blood sample was obtained by veinous punction, and the white blood cells were separated from other blood components. For example, Ficoll-Paque from Farmacia was used to obtain blood lymphocytes and other mononuclear cells. The cells were suspended at 10$^7$ cells/ml and lysed with the Nonidet P40 containing buffer as described in Example 1. Aliquots (5–10 µl) of the lysate were mixed with poly(-rI):(rC)-agarose or sepharose beads and these were incubated with [$^{32}$P]-ATP as described in Example 2. The amounts of (2'-5') oligo-isoadenylate produced were measured by high voltage electrophoresis, or by the alumina column procedure of Example 2.

The data reported in Table 3 show the variations in the level of oligo-isoadenylate synthetase observed in human white blood cells under different pathological conditions. It appears clearly that in two different forms of acute leukemia, the values obtained are 10 times lower than in normal blood. In a third form of acute leukemia the values were only slightly lower than normal. In chronic lymphatic leukemia, low values were seen, but which were higher than in acute lymphatic leukemia. In one type of autoimmune disease, namely lupus erythematosus there was an increased enzyme level.

Incubation of the leukemic cells with interferon is able to bring the level of oligo-isoadenylate back to normal (Table 3). The herein described enzyme assays would, therefore, be very valuable to follow the response of these leukemic patients to interferon therapy. The measurements can be done on small amounts of blood (less than 2 ml) and within less than 24 hours. The assay can be used for various types of blood cells and for other tissues. The pathological conditions of interest would include cancer, infectious diseases and immunological disorders.

Example 4: Kit for Interferon Assay a. Protein kinase assay: the reagents required to carry out this assay are:
   (1). Lysis buffer (0.5% Nonidet P40, 20 mM Hepes-HCl buffer pH 7.5, 5 mM MgCl$_2$, 120 mM KCl, 1 mM dithiothreitol, 10% glycerol).
   (2). Poly(rI):(rC)-adenosine triphosphate (ATP) mixture (in concentrated form).
   (3). Purified rabbit protein eIF2 (over 100 μg/ml)
   (4). [$^{32}$P]-γ-ATP (over 10 Ci/mmole, and 1 mCi/ml)

These are provided in a kit form. The above were provided freeze dried and can be dissolved according to indications prior to use. Plates to grow the cells are available from Nunc Company. Commercial equipment for polyacrylamide gel electrophoresis and X-ray films are available from commercial companies. Standard solution of interferons (e.g. mouse, human etc.,) are included in kit for calibration curves.

b. Oligo-isoadenylate synthetase assay:
The reagents required are:
   (1). Lysis buffer
   (2). Sepharose bound poly (rI):(rC)
   (3). [$^{32}$P]-α-ATP (over 3 Ci/mmol and 1 mCi/ml)
   (4). Bacterial alkaline phosphatase
   (5). 2'-5' diadenosine monophosphate 2'-5' triadenosine diphosphate.
   (6). Small disposable columns containing 0.3 ml of alumina.
   (7). Alumina elution buffer: 1 M glycine, 0.75 N HCl, pH 2.

These reagents are provided in a kit as above. Paper electrophoresis and thin layer chromatography equipment needed is commonly available.

The amounts of reagent needed are provided invariable amounts according to the number of determination the user desires to perform.

TABLE 1

INTERFERON-INDUCED ENZYMES AND ANTIVIRAL STATE IN L CELLS

| Interferon U/ml | VSVRNA | Protein kinase PKi | Oligo-isoadenylate synthetase E | Phosphodiesterase 2'-PDi |
|---|---|---|---|---|
| 0 | 100 | 15 | 4 | 25 |
| 2 | 20 | 35 | 5 | 72 |
| 10 | 5 | 80 | 20 | 86 |
| 50 | 2 | 100 | 42 | 100 |
| 250 | 0 | | 66 | |
| 1250 | 0 | | 100 | 100 |

Results are in percent of maximum activity. Cells were treated for 8 hours with interferon. Enzyme assays are as described in the text. Measure of Vesicular Stomatitis Virus (VSV) RNA synthesis as in Weissenbach et al (European J. Biochem. 197, 98 1-8).

TABLE 2

KINETICS OF ENZYME INDUCTION BY INTERFERON

| Time after interferon addition | Mouse L cells* Protein kinase PKI | Human fibroblasts** oligo-isoadenylate synthetase |
|---|---|---|
| Hours | Phosphorylation of the 35,000 Mr subunit of eIF2, arbitrary units | (2'-5') oligo A synthesized counts/min |
| 0 | 15 | 900 |
| 2 | 15 | 900 |
| 4 | 30 | 1,500 |
| 8 | 55 | 3,750 |
| 10 | 75 | 6,500 |
| 24 | 100 | 13,500 |

*with 200 units/ml mouse interferon
**with 50 units/ml human fibroblast interferon.

TABLE 3

VARIATIONS IN THE LEVEL OF OLIGO-ISOADENYLATE ACTIVITY IN HUMAN WHITE BLOOD CELLS UNDER DIFFERENT PATHOLOGICAL CONDITIONS

| Blood source | Oligo-isoadenylate synthetase [$^{32}$P](2'-5') oligo A, cpm × 10$^{-3}$ |
|---|---|
| Normal donors | 200-240 |
| Acute lymphatic leukemia | 20-25 |
| Chronic lymphatic leukemia | 50-70 |
| Acute Monocytic leukemia | 160-200 |
| Acute Myeloid leukemia | 20 |
| Same incubated o.n. with human interferon* | 200 |
| Lupus erythematosus | 270-300 |

Procedure: 2 ml blood → Ficoll gradient → 10$^7$ leucocyte cells/ml → lysis with NP40 → binding to agarose-poly(rI):(rC) beads → incubation with [$^{32}$P]-ATP → analysis of (2'-5') oligo A by high voltage electrophoresis or alumina columns.
*human leukocyte interferon 500 Units/ml

We claim:
1. An assay for the quantitative determination of interferon, without the necessity of viral infection, consisting essentially of the steps of extracting a cell previously exposed to said interferon by means of a non-ionic surfactant, and determining in such extract the quantity of protein kinase (PK-i), oligo-isoadenylate synthetase, or phosphodiesterase, the content of which in said cell is a function of the quantity of interferon to which said cell has been previously exposed.

2. An assay according to claim 1, further including, prior to said extractant step, adding a substrate, which is to be assayed as to its interferon content, to a cell culture and using said cell culture, after a predetermined period of time, as said cells being extracted, the quantity of enzyme determined by said determining step being indicative of the interferon content of the substrate.

3. An assay according to claim 2 wherein the cell culture used is one of leukocytes, lymphocytes, human fibroblasts, or mouse L cells.

4. An assay according to claim 1 or 2 wherein the enzyme assay is carried out by incorporation of radioactive markers and determination of these.

5. An assay according to claim 2, wherein the cells are extracted after from 3 to 24 hours of exposure of the cell culture to said substrate.

* * * * *

UNITED STATES PATENT AND TRADEMARK OFFICE
CERTIFICATE OF CORRECTION

PATENT NO. : 4,302,533
DATED : November 24, 1981
INVENTOR(S) : REVEL et al.

It is certified that error appears in the above-identified patent and that said Letters Patent are hereby corrected as shown below:

Column 2, line 20, after "ether" insert --)--
Column 3, line 9, change "ng" to --µg--
Column 5, lines 46-47, change "invariable" to --in variable--

Signed and Sealed this

Thirtieth Day of March 1982

[SEAL]

Attest:

Attesting Officer

GERALD J. MOSSINGHOFF
Commissioner of Patents and Trademarks